United States Patent
Broyles et al.

(10) Patent No.: US 12,336,878 B2
(45) Date of Patent: Jun. 24, 2025

(54) DENTAL CROWN HAVING A HIGHLY RETENTIVE COATING AND METHOD FOR MAKING THE SAME

(71) Applicant: Solventum Intellectual Properties Company, Maplewood, MN (US)

(72) Inventors: Bruce R. Broyles, Oakdale, MN (US); Afshin Falsafi, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/492,179

(22) Filed: Oct. 23, 2023

(65) Prior Publication Data
US 2024/0050196 A1    Feb. 15, 2024

Related U.S. Application Data

(63) Continuation of application No. 16/761,325, filed as application No. PCT/IB2018/058590 on Nov. 1, 2018, now abandoned.
(Continued)

(51) Int. Cl.
*A61C 5/77* (2017.01)
*A61C 13/00* (2006.01)
(Continued)

(52) U.S. Cl.
CPC ............... *A61C 5/77* (2017.02); *A61K 6/84* (2020.01); *A61K 6/887* (2020.01);
(Continued)

(58) Field of Classification Search
CPC ... A61C 5/77; A61C 13/0021; A61C 13/0022; A61K 6/84; Y10T 29/49567; Y10T 29/49888; B23K 20/02
See application file for complete search history.

(56) References Cited

U.S. PATENT DOCUMENTS 3,969,480 A * 7/1976 Fedor .................... F01N 3/2842
                                                     502/527.22
4,068,379 A   1/1978 Miller et al.
(Continued)

FOREIGN PATENT DOCUMENTS

CN      1163093 A     10/1997
DE      3435918 A1    4/1986
(Continued)

OTHER PUBLICATIONS

Rusnaldy: "Diffusion Bonding : An Advanced of Material Process", Rotasi, vol. 3, No. 1, Jan. 2001 (Jan. 2001), pp. 23-27, Retrieved from the Internet: URL:https://ejournal.undip.ac.id/index.php/rotasi/article/view/2487/2199 (Apr. 12, 2024).
(Continued)

*Primary Examiner* — Jermie E Cozart

(57) ABSTRACT

Dental crowns and methods of making the same. The dental crown may include a metal shell shaped to cover a portion of a tooth of a patient; a coating retention metal layer diffusion bonded to the metal shell, wherein an interface between the coating retention layer and the metal shell comprises a plurality of interstitial regions; and a composition on the coating retention layer and within the plurality of the interstitial regions to bond the coating composition to the metal shell.

20 Claims, 11 Drawing Sheets

Related U.S. Application Data

(60) Provisional application No. 62/582,100, filed on Nov. 6, 2017.

(51) Int. Cl.
*A61K 6/84* (2020.01)
*A61K 6/887* (2020.01)
*B23K 20/02* (2006.01)

(52) U.S. Cl.
CPC ...... *A61C 13/0021* (2013.01); *A61C 13/0022* (2013.01); *B23K 20/02* (2013.01); *Y10T 29/49567* (2015.01); *Y10T 29/49888* (2015.01)

(56) References Cited

U.S. PATENT DOCUMENTS

| | | | |
|---|---|---|---|
| 4,273,580 A | 6/1981 | Shoher et al. | |
| 4,364,731 A | 12/1982 | Norling et al. | |
| 4,392,829 A | 7/1983 | Tanaka | |
| 4,398,887 A | 8/1983 | Balde et al. | |
| 4,698,021 A | 10/1987 | Shoher et al. | |
| 4,722,689 A | 2/1988 | Corbett | |
| 4,834,656 A | 5/1989 | Loudon | |
| 4,846,718 A | 7/1989 | Rieger | |
| 5,186,626 A | 2/1993 | Tanaka | |
| 5,342,201 A | 8/1994 | Oden | |
| 5,722,826 A * | 3/1998 | Tuneberg | A61C 7/16 433/9 |
| 6,106,295 A | 8/2000 | Wilson | |
| 6,129,261 A * | 10/2000 | Sanders | B23K 20/02 228/157 |
| 6,663,390 B2 | 12/2003 | Riley et al. | |
| 7,008,229 B2 | 3/2006 | Stoller et al. | |
| 8,597,762 B2 | 12/2013 | Clunet-Coste et al. | |
| 9,044,292 B2 | 6/2015 | Velamakanni et al. | |
| 9,370,404 B2 | 6/2016 | Velamakanni et al. | |
| 2004/0109783 A1 | 6/2004 | Prasad et al. | |
| 2009/0286205 A1 | 11/2009 | Johnson et al. | |
| 2010/0081110 A1 | 4/2010 | Mayer et al. | |
| 2010/0203480 A1 | 8/2010 | Schweitzer et al. | |
| 2011/0230973 A1* | 9/2011 | Hippensteel | A61L 27/56 228/173.6 |
| 2013/0004917 A1 | 1/2013 | Mayer et al. | |
| 2013/0130203 A1 | 5/2013 | Velamakanni et al. | |
| 2013/0137064 A1 | 5/2013 | Velamakanni et al. | |
| 2017/0333158 A1 | 11/2017 | Mancini | |
| 2018/0085490 A1 | 3/2018 | Kay et al. | |

FOREIGN PATENT DOCUMENTS

| | | |
|---|---|---|
| DE | 3600977 A1 | 8/1986 |
| DE | 3600977 C2 | 2/1990 |
| EP | 0051704 A1 | 5/1982 |
| EP | 0051704 B1 | 7/1985 |
| EP | 0156273 A2 | 10/1985 |
| SU | 1237197 A1 | 6/1986 |
| WO | 200110332 A1 | 2/2001 |
| WO | 2003078508 A1 | 9/2003 |
| WO | 2007097747 A1 | 8/2007 |
| WO | 2008080239 A1 | 7/2008 |
| WO | 2012021442 A1 | 2/2012 |
| WO | 2012021442 A9 | 2/2013 |

OTHER PUBLICATIONS

DIN8584-3, Din Deutsches Institut Fur Normung E. V, Sep. 2003 (Sep. 2003), Berlin, pp. 1-15, XP009510301.
International Search Report for PCT International Application No. PCT/IB2018/058590, mailed on Jan. 21, 2019, 5 pages.

* cited by examiner

DENTAL CROWN HAVING A HIGHLY RETENTIVE COATING AND METHOD FOR MAKING THE SAME

CROSS REFERENCE TO RELATED APPLICATIONS

This application is a continuation of U.S. application Ser. No. 16/761,325, filed May 4, 2020, currently pending, which is a 371 of PCT/IB2018/058590, filed Nov. 1, 2018, which claims priority from U.S. Provisional Application Ser. No. 62/582,100, filed Nov. 6, 2017, the disclosures of which are incorporated by reference in their entireties herein.

BACKGROUND

Preformed stainless-steel crowns are still the preferred choice for whole or partial replacements of teeth. They are a very durable and reliable restoration for a tooth in need of complete coverage. However, stainless-steel crowns have an unattractive appearance. Thus, there is a need for stainless-steel dental crowns that have a more natural look with preferably a more natural look with a tooth-like appearance. Various dental crowns and methods of making dental crowns are disclosed, for example in: U.S. Pat. Nos. 4,068,379; 6,663,390; 6,106,295; 7,008,229; 8,597,762; 9,044,292; U.S. Patent Publication 2009/0286205 Chinese Pat. No. 1,163,093; European Pat. No. 0156273; European Pat. No. 0051704; and German Patent Publication 3600977. However, it is always desirable to create better solutions for creating long lasting dental crowns.

SUMMARY

Some aspects of the present disclosure provide a dental crown. The dental crown could include a metal shell shaped to cover a portion of a tooth of a patient; a coating retention metal layer diffusion bonded to the metal shell, wherein an interface between the coating retention layer and the metal shell comprises a plurality of interstitial regions; and a composition on the coating retention layer and within the plurality of the interstitial regions to bond the coating composition to the metal shell.

Some other aspects of the present disclosure provide another dental crown. The dental crown could include a continuous, nonporous metal shell shaped to cover a portion of a tooth of a patient; a coating retention metal layer of elongated metal strands bonded to the metal shell, wherein there are apertures between the elongated metal strands, wherein the apertures between the elongated metal strands comprise 10 to 60 percent of the area of the coating retention layer, and wherein an interface between the coating retention layer and the metal shell comprises a plurality of interstitial regions; and a polymeric composition on the coating retention layer and within a plurality of the interstitial regions to bond the coating composition to the metal shell.

Some aspects of the present disclosure provide a method of forming a dental crown. The method may include diffusion bonding a metal base layer to a coating retention layer to form a dental crown blank, wherein the coating retention layer comprises a plurality of apertures wherein an interface between the metal base layer and the coating retention layer comprises a plurality of interstitial regions; coating a composition on the coating retention layer and within the plurality of the interstitial regions to bond the coating composition to the metal base layer; and forming the dental crown blank into a dental crown shaped to cover at least a portion of a tooth of a patient.

Some other aspects of the present disclosure provide a method of forming a dental crown. The method may include bonding a continuous, nonporous metal base layer to a coating retention layer to form a dental crown blank, wherein the coating retention layer comprises a plurality of apertures wherein an interface between the metal base layer and the coating retention layer comprises a plurality of interstitial regions, wherein the plurality of apertures between the elongated metal strands comprise 10 to 70 percent of the area of the coating retention layer; and coating a composition on the coating retention layer and within the plurality of the interstitial regions to bond the coating composition to the metal base layer; and forming the dental crown blank into a dental crown shaped to cover at least a portion of a tooth of a patient.

The details of one or more examples of this disclosure are set forth in the accompanying drawings and the description below. Other features, objects, and advantages of this disclosure will be apparent from the description and drawings, and from the claims.

DETAILED DESCRIPTION

There has been a long-standing need for both temporary and permanent esthetic metal crowns for dental patients.

Figure 1:
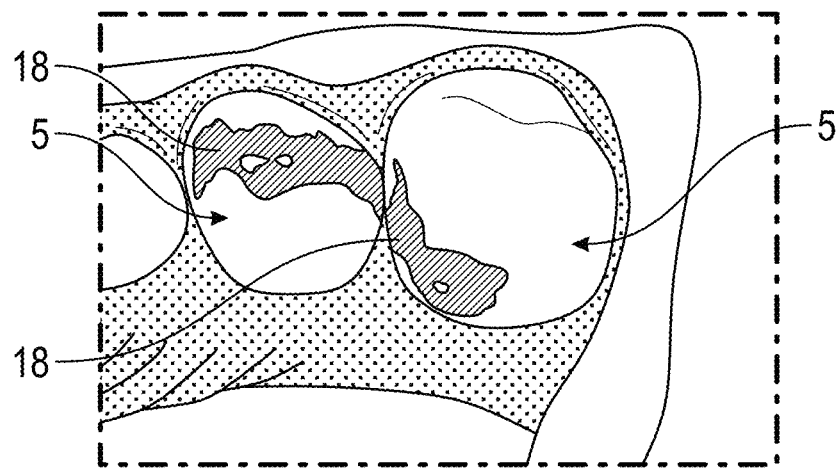
FIGS. 1 and 2 illustrate prior art dental crowns, where the esthetic coating has delaminated from the stainless-steel crowns.
Figure 2:
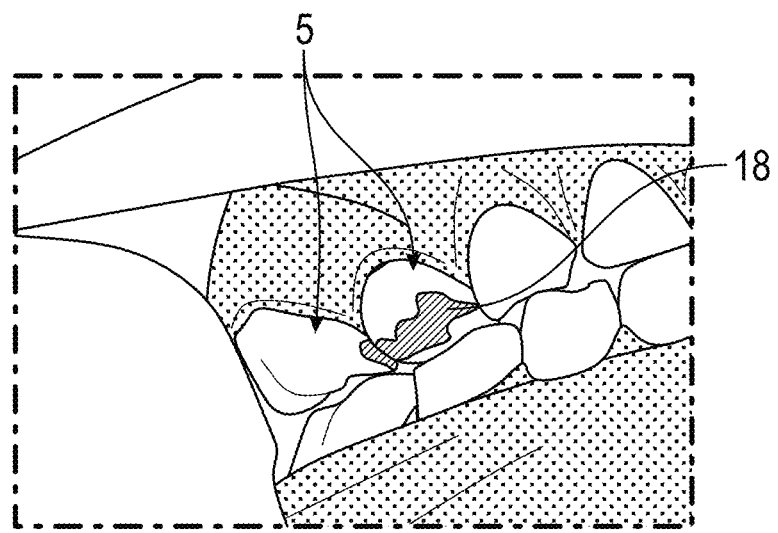

Traditionally, dental patients have received dental crowns made from stainless steel because they are very durable and provide reliable restorations for the patient's tooth. However, stainless steel crowns have an unattractive appearance. Thus, there is a need for stainless steel dental crowns that have a more natural look with preferably a tooth-like color. Attempts have been made using resins, such as polyesters, epoxies, acrylics, and high-density polyethylene, to form an esthetically pleasing appearance on the outside of the crown. But, as illustrated by FIGS. 1 and 2, as these crowns contact other teeth or dental work, as well as food items placed in the mouth, the outside coatings 18 tend to be sheared off because of this contact and the resultant forces of occlusion.

Figure 3:
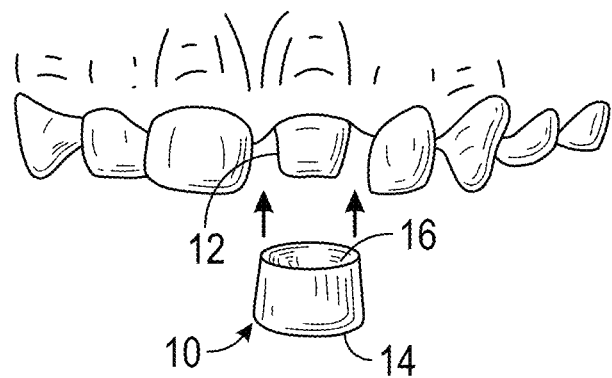
FIG. 3 illustrates an esthetic dental crown of the present invention as it is being placed on a tooth that is prepared to receive it.
Figure 4:
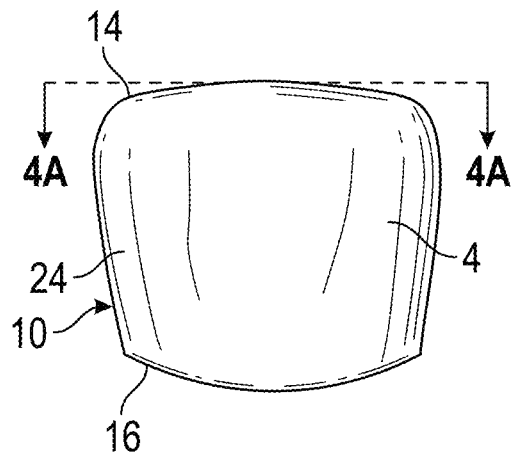
FIG. 4 is an elevational front (facial) view of an esthetic dental crown illustrated in FIG. 1.
Figure 5:
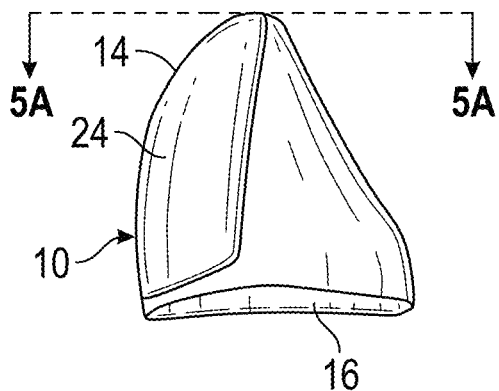
FIG. 5 is an elevational profile (interproximal) view of another esthetic dental crown of the present invention.
Figure 5A:
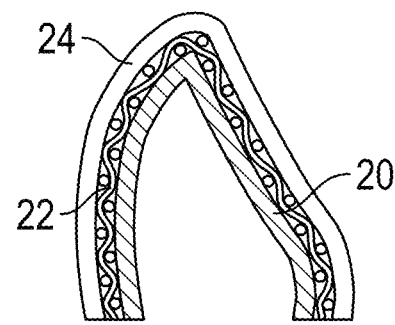
FIG. 5A is a cross-sectional view taken along line 5A-5A in FIG. 5.

FIGS. 3-5 illustrate exemplary examples of the esthetic dental crown of the present invention. Dental crown 10 is being shown in FIG. 1 as it is being placed in the mouth to cover a prepared tooth 12. The prepared tooth 12 is shown as having its surface ground away sufficiently for the placement of the crown 10 thereon.

The scale of the teeth shown and the crown 10 to be placed thereon is for ease of illustration and should not be considered to be at the correct scale. Furthermore, the portion of the tooth 12, which has been ground away, is also for illustration purposes only.

Figure 4A:
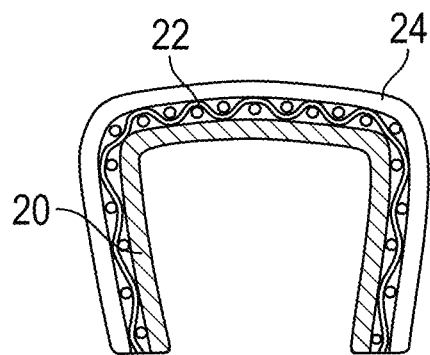
FIG. 4A is a cross-sectional view taken along line 4A-4A in FIG. 4.

FIGS. 4 and 4A are convenient for illustrating the various layers that are used to create a laminate used in the dental crown 10. The dental crown has an occlusal surface 14 and an open end 16 opposite the occlusal surface 14 for receiving the prepared tooth 12. The dental crown is shaped to resemble the original tooth it replaces, and the open end 16 is for placement over the prepared tooth 12. It is sized to fit comfortably over the portion of the tooth 12 on which the dental procedure is being performed. The crown is trimmed so that the bottom edge of the crown meets the gum line in a comfortable manner approximating the placement of the tooth when the crown 10 is applied. The crowns 10 are manufactured in various size and shapes to fit different types of teeth. The crown 10 is malleable so it can be crimped around the base of the tooth and shaped on the occlusal surface to provide a comfortable bite with the opposing tooth. However, the coating 24 is retained on the crown 10 during this crimping and shaping steps. Proper tooth preparation includes removing all caries and proper shaping the remaining natural tooth to receive the dental crown 10.

The dental crown 10 has a metal layer or foil 20, shown as a metal shell. The metal for the shell 20 is preferably stainless steel, but also could be aluminum, tin, silver, gold and any alloys thereof. The metal layer is preferably a continuous layer and nonporous. This is to prevent the coating material from seeping into the interior of the crown, which might interfere with the crown preparation and placement. The dental crown 10 has a coating retention layer 22. The retention layer 22 is preferably stainless steel, but also could be aluminum, tin, silver, gold and any alloys thereof. The retention layer keeps the coating 24 highly retained on the metal shell 20, even after long periods of use. Due to the mechanical structure of the retention layer, the coating 24 is strongly adhered to the metal shell 20, as described in more detail below relative to FIGS. 9 through 10. When the dental crown 10 is shaped and crimped prior to placement, the esthetic coating layer 24 does not delaminate or sheer off. Likewise, as the dental crown 10 receives various occlusal forces from the opposing teeth or food, the esthetic coating layer 24 does not delaminate or shear off from the crown 10.

In one exemplary embodiment, the coating retention layer 22 is made from a mesh of intermingled, elongated strands of metal. The metal strands 26 may be woven into a variety of patterns. Examples of some patterns are illustrated in FIGS. 18A-D. Alternatively, the metal strands 26 may be arranged in a nonwoven mesh. Regardless, the open spaces between adjacent metal strands 26 create apertures 30 within the coating retention layer 22.

FIG. 4 shows a molar crown 10. FIG. 5 shows an eyetooth crown 10. However, it is understood that the present invention is applicable to both anterior and posterior crowns as well. The present invention provides a dental crown 10 that may be suitable for all types of crowns that could be used by a prospective dental patient, which are long lasting.

Figure 6:
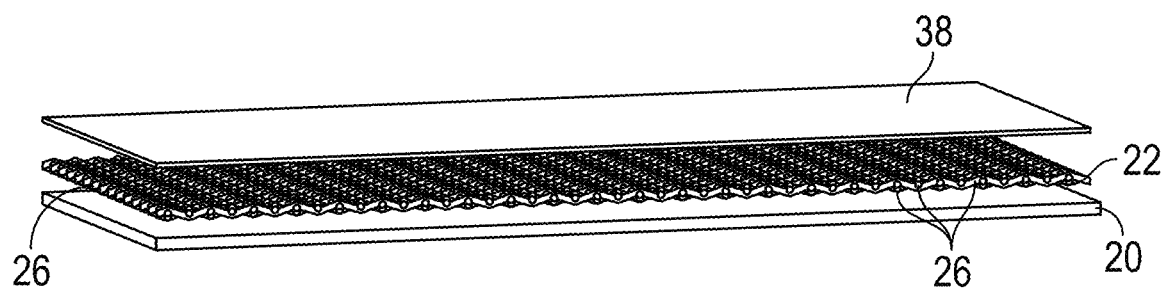
FIG. 6 illustrates layers used to make a laminate for use in a dental blank.
Figure 8:
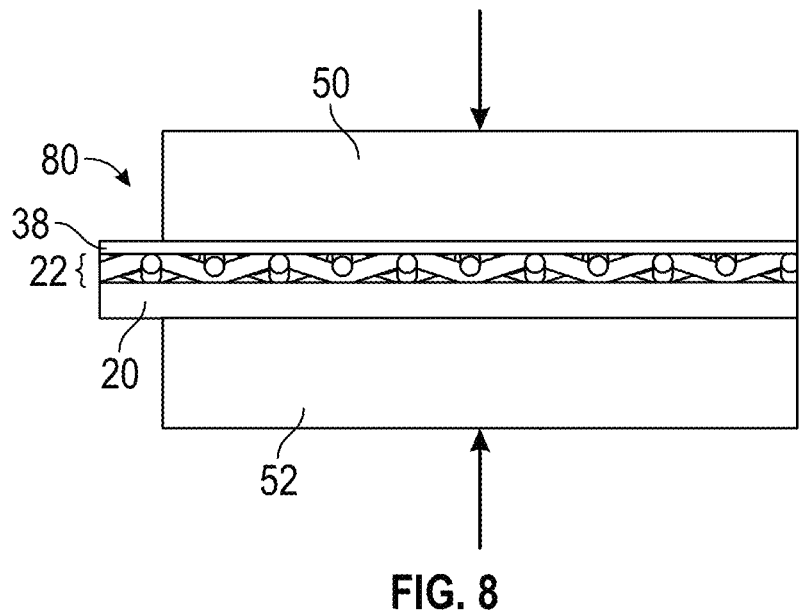
FIG. 8 illustrates one embodiment of a schematic view of bonding the metal layer to the coating retention layer.

FIG. 6 is convenient for illustrating the various layers used for making the laminate in the dental crown 10 of the present invention during the diffusion bonding portion of the method. A metal layer or foil 20 is brought into contact with a coating retention layer 22. A separator sheet 38 is brought into contact with the coating retention layer 22. A stack 80 of these three layers is then heated in a furnace while being forced together in a press, as illustrated in FIG. 8 and discussed more below, to bond the metal layer 20 and coating retention layer 22. Thereafter, the separator sheet 38 is removed, and thus a laminate for a dental blank is created.

Figure 7:
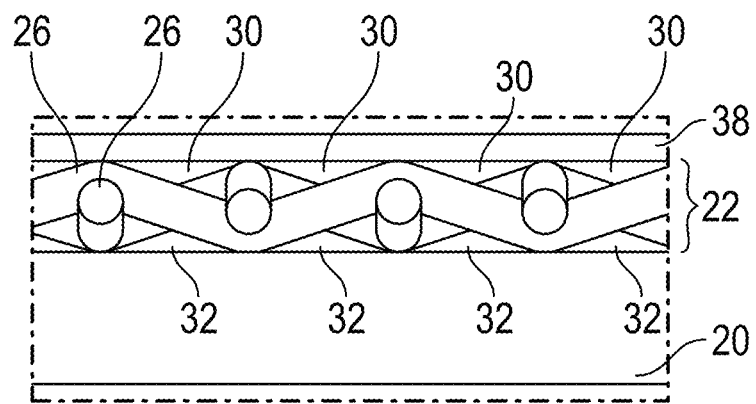
FIG. 7 illustrates a magnified view of the layers to make a laminate for use in a dental blank.
Figure 9:
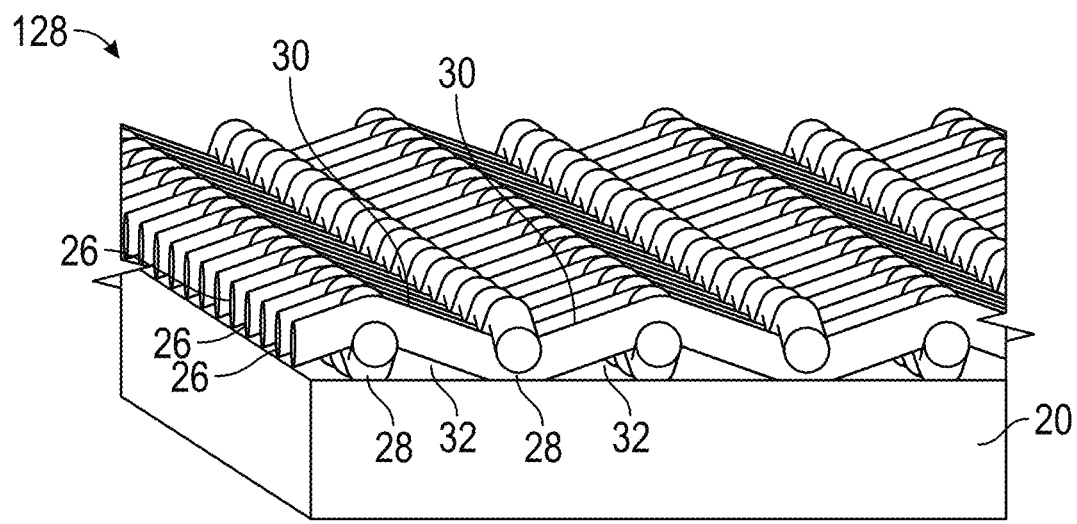
FIG. 9 illustrates a magnified view of the layers after bonding.

FIG. 7 shows a magnified view of the metal layer 20 and coating retention layer 22 prior to this diffusion bonding process and FIG. 9 shows a magnified view after the diffusion bonding process.

As illustrated in FIGS. 7 and 9, when the metal layer 20 is adjacent to the coating retention layer 22, the interface between the two creates a plurality of interstitial regions 32. These open spaces provide regions for conveniently receiving the polymeric composition 24, when it is applied over the coating retention layer 22, described in more detail below. The interstitial regions 32 underlie at least a portion of the metal strands 26, but ideally underlie the majority of the metal strands 26.

One exemplary embodiment for diffusion bonding the metal layer 20 to the coating retention layer 22 is shown in FIG. 8. The stack 80 of metal layer 20, retention layer 22, and separator sheet 38 put into a hot press furnace having two opposing plates 50, 52. The stack 80 is heated by the furnace and the plates 50 and 52 apply pressure. The time and temperature is picked to allow the metal layers 20, 22 to diffuse into each other at the points of contact, but to still maintain the interstitial regions 32. For example, if the metal layer 20 is made of stainless steel and the retention layer 22 is made of stainless steel, the furnace may be heated within a range of 300 to 900° C. Other metals, temperatures, pressures, and times may be selected by known by one skilled in the art.

Alternatively, other bonding processes may be used, other than diffusion bonding. For instance, welding or brazing may be used to bond the coating retention layer 22 to the metal base layer 20, while still maintaining the interstitial regions 32 between the two layers.

FIG. 9 shows a magnified picture of the retention layer 22 and the metal base layer 20 after the diffusion bonding step. As illustrated, the portion of the metal strands 26 adjacent to the metal base layer 20 have melted with the metal base layer to create bonded areas 28. Adjacent the top surface of the metal base layer 20 and underlying the metal strands 26 are the interstitial regions 32.

Figure 10:
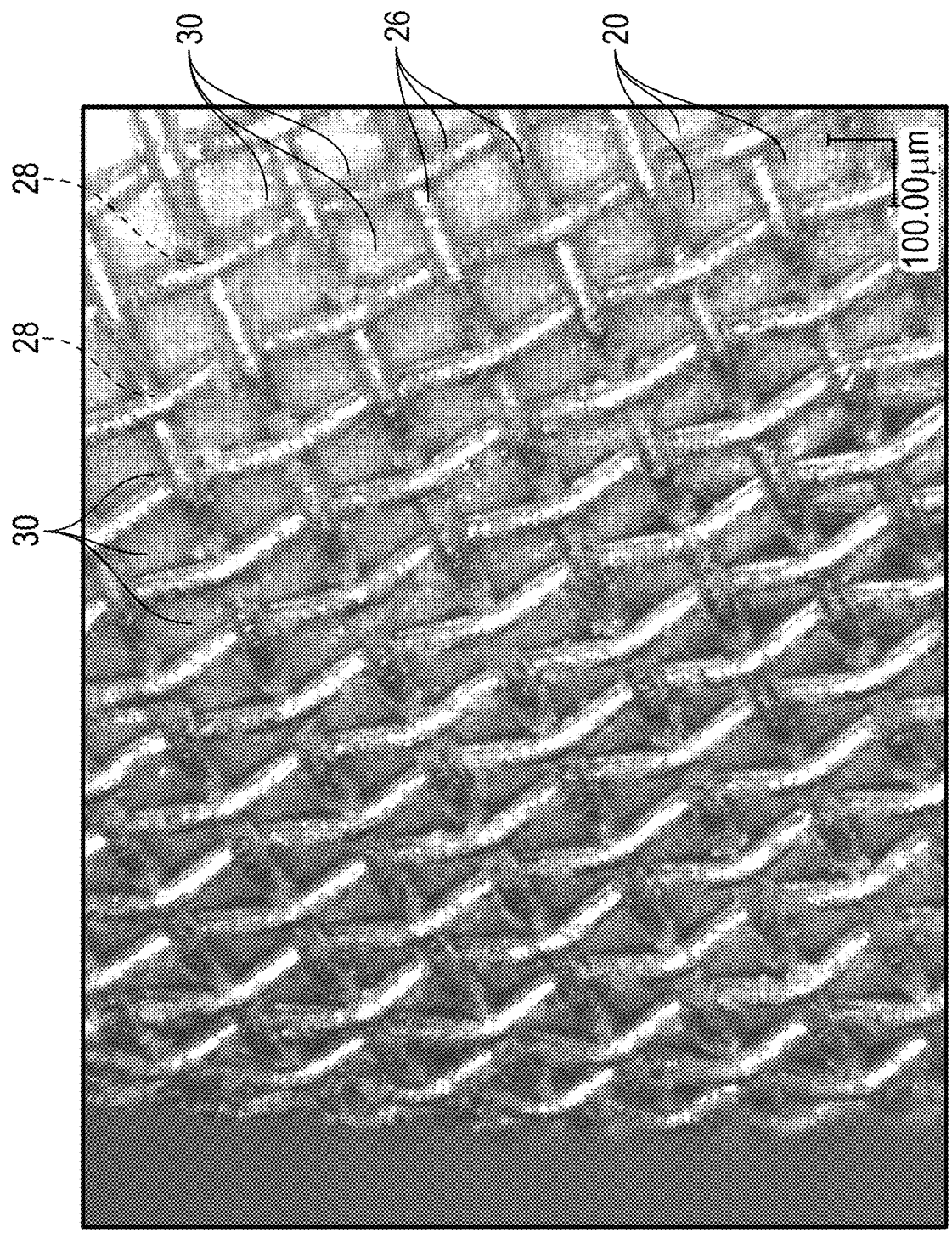
FIG. 10 illustrates a magnified picture of the layers after bonding.
Figure 11:
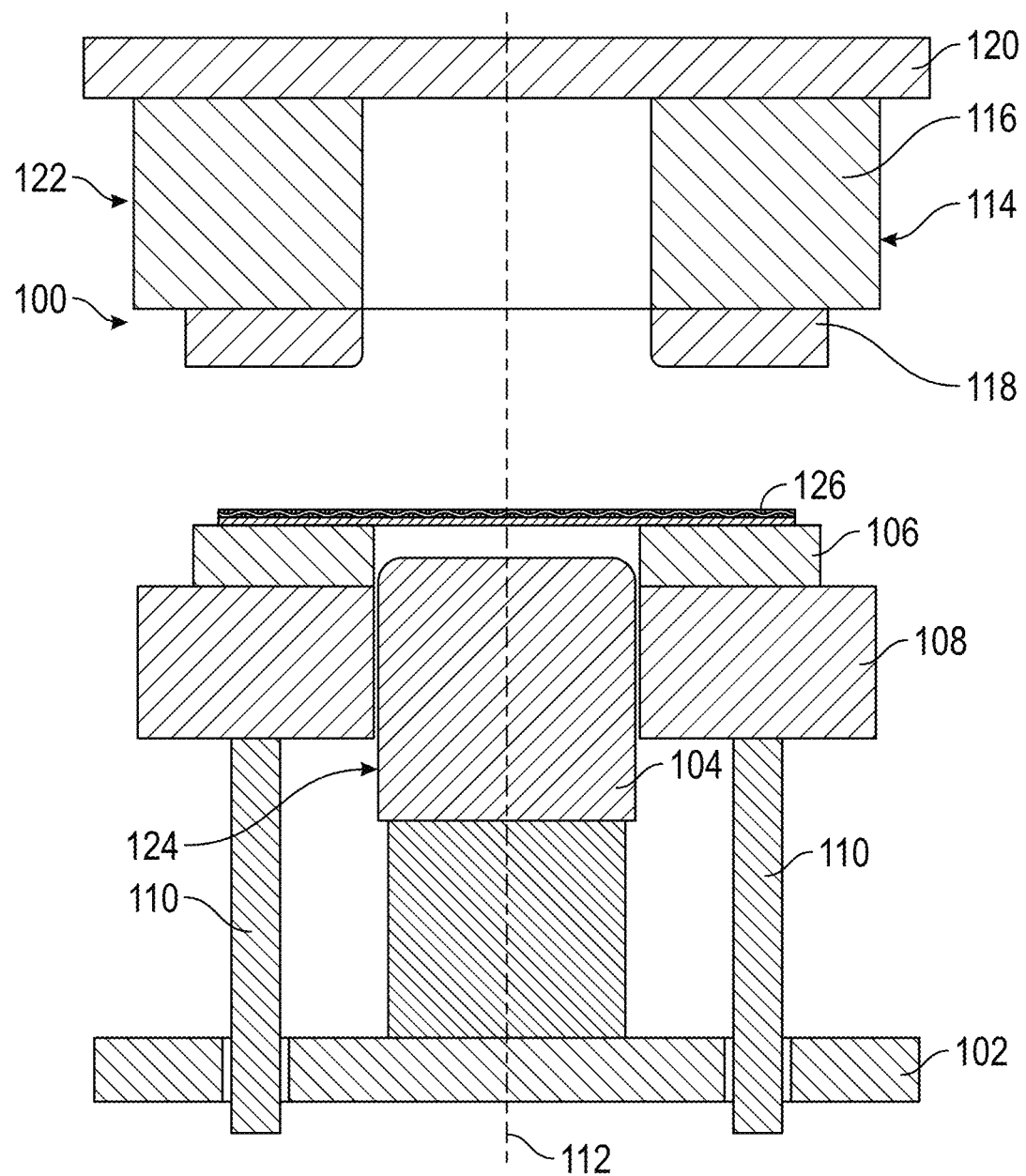
FIGS. 11-14 show schematic cross-sections through the deep-drawing die in the four different phases of a deep-drawing process.

FIG. 10 illustrates a magnified picture of the layers after the bonding process described above. Each of the metal strands 26 in the coating retention layer 22 are bonded to the base metal layer 20 in areas 28. Between the metal strands 26 are apertures 30. In one embodiment, the coating retention layer 22 is selected so that the plurality of apertures 30 contribute 10 to 60 percent of the total area of the coating retention layer 22. In another embodiment, the coating retention layer 22 is selected so that the plurality of apertures 30 contribute 30 to 60 percent of the total area of the coating retention layer 22. In one example, a coating retention layer 22 with an 80 mesh with a 4-mil (94 micrometer diameter) wire gauge provides 46% area of apertures or open area. The number of apertures 30 may be optimized to allow enough open area for the composition 24 to sufficiently bond to the metal layer 20 and to flow into the interstitial regions 32 for additional bonding areas and around the metal strands 26. The number of apertures 30 may also be optimized to provide enough metal strands 26 to sufficiently bond with the metal layer 20. The gauge of the metal strands 26 may also be optimized to sufficiently bond with the metal layer 20.

After the dental blank is created, it is then formed into a dental crown by deep drawing the blank with a series of forming dies. One exemplary process for deep drawing is according to process DIN 8585-3.

A deep-drawing die illustrated schematically in FIGS. 11 to 14, which is convenient for illustrating the method step for converting the dental blank into a dental crown 10.

The deep-drawing die set 100 includes a base plate 102, a drawing punch 104 arranged stationarily on the upper side of the base plate 102, and a sheet-metal holder 106 which surrounds the drawing punch 104 in a ring shape and is arranged on a supporting plate 108 which likewise surrounds the drawing punch 104 in a ring shape and is borne by spindle sleeves 110 which can be moved vertically be means of a hydraulic moving device (not illustrated) so that the supporting plate 108 can be moved with the sheet metal holder 106 arranged thereon along the vertical direction drawing 112.

The deep-drawing die set 100 also includes a drawing member 114 which is arranged above the drawing punch 104 and the sheet metal holder 106 and comprises, for its part, a ring-shaped drawing ring support 116 and a drawing ring 118 held on its underside.

The drawing ring support 116 is held at its upper side on a holding plate 120 which can be moved by means of a hydraulic moving device (not illustrated) along the direction of drawing 112 relative to the drawing punch 104 and the sheet metal holder 106.

The drawing member 114 forms the first deep-drawing die part 122 of the deep-drawing die set 100; the drawing punch 104 forms the second deep-drawing die part 124 of the deep-drawing die set 100.

A first deep-drawing process is carried out as follows with the deep-drawing die set 100 described above.

First, the drawing member 114 and the sheet metal holder 106 are displaced into their respective upper starting positions by means of the respective hydraulic moving devices (not illustrated).

In the upper starting position of the sheet metal holder 106, the essentially flat upper side of the sheet metal holder 106, the essentially flat upper side of the sheet metal holder 106 is arranged above the upper side of the drawing punch 104.

Figure 12:
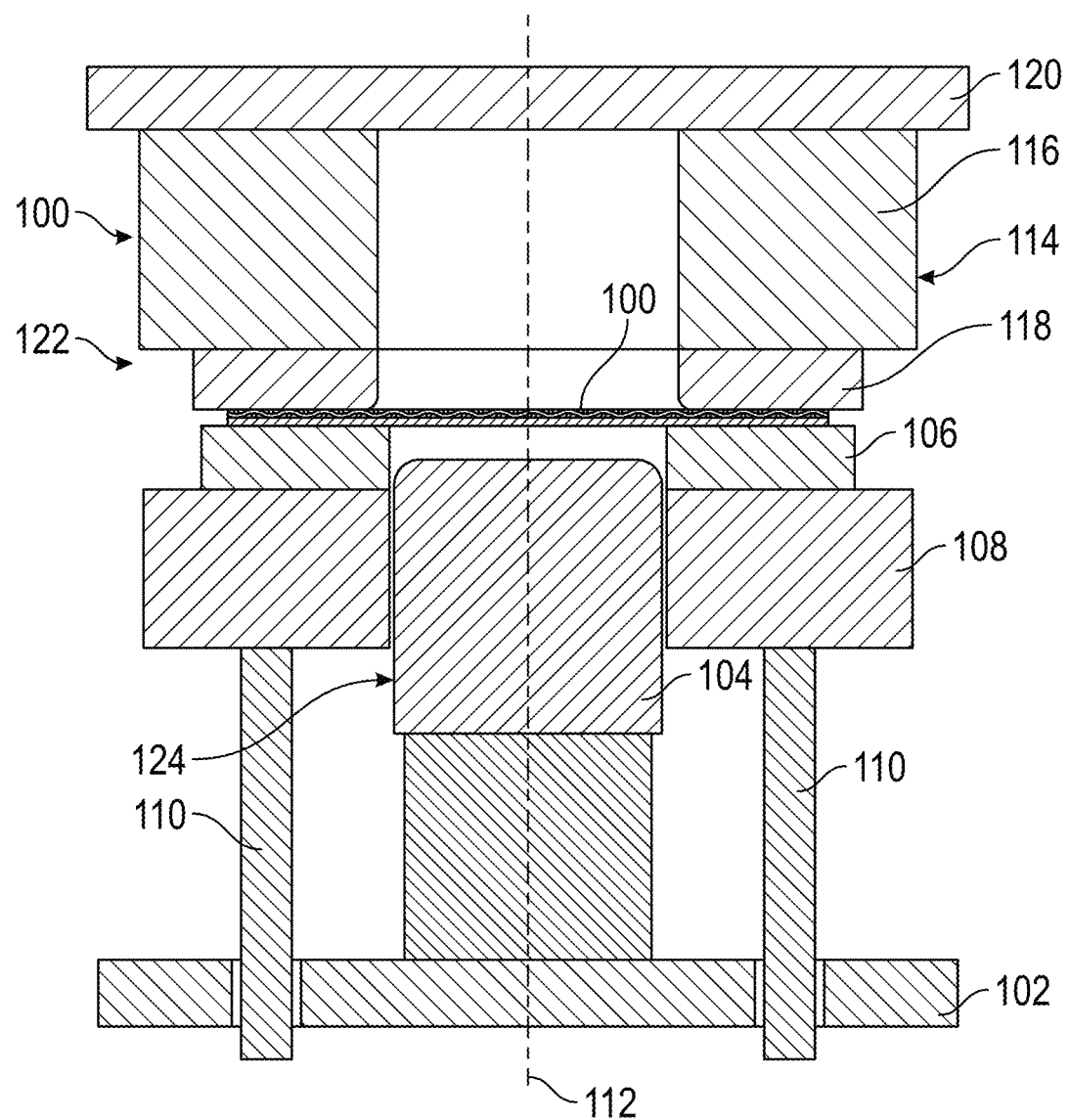

In this position, the dental blank 126, from which the drawn part is intended to be produced, is inserted into the deep-drawing die set 100 such that the edge of the blank 126 rests on the sheet metal 106, as illustrated in FIG. 12.

Figure 13:
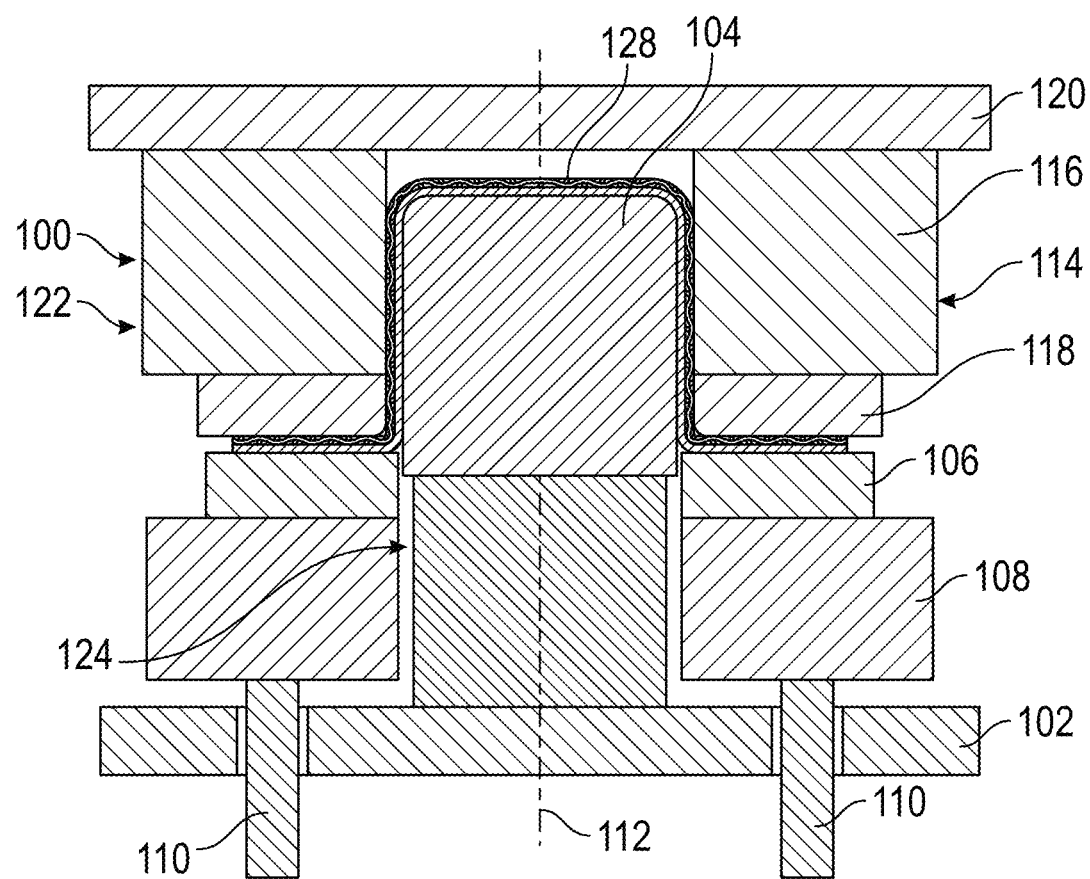

Subsequently, the deep-drawing die set 100 is closed in that the drawing member is displaced by means of the hydraulic moving device (not illustrated) downwards out of its upper starting position to such an extent along the direction of drawing 112 until the underside of the drawing ring 118 on the upper side of the blank 126 and the edge of the blank 126 is clamped between the drawing ring 118 and the sheet metal holder 106, as illustrated in FIG. 13.

Figure 14:
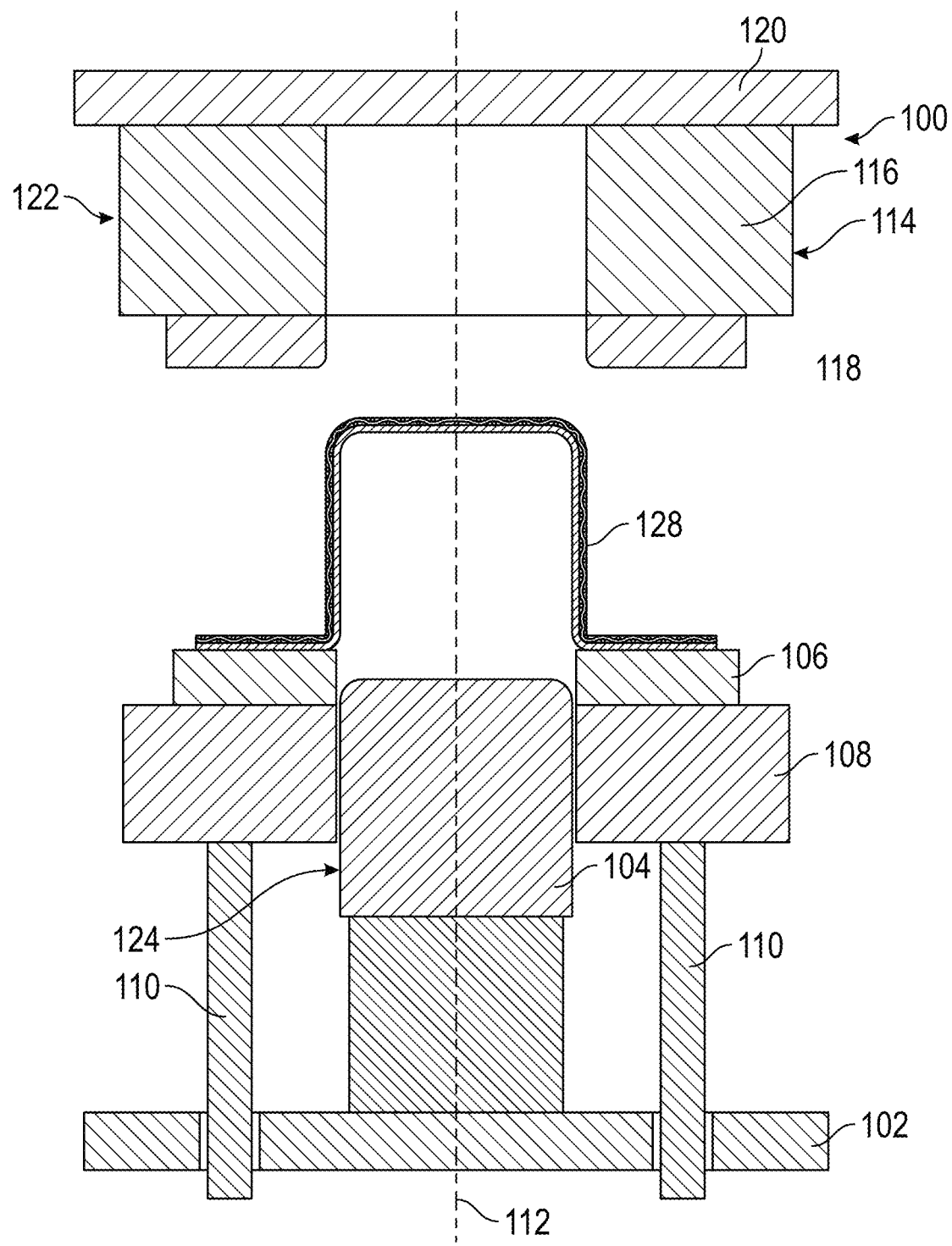

In the subsequent method step, the blank 126 is formed into a drawn part 128 in that the spindle sleeves 110 with the supporting plate 108 arranged thereon and the sheet metal holder 106 as well as the drawing member 114 are moved downwards by means of the hydraulic moving device (not illustrated) along the direction of drawing 112 relative to the drawing punch 104 by the drawing depth, wherein the blank 126 held securely at its edge between the drawing ring 118 and the sheet metal holder 106 fits closely along the outer contours of the drawing ring 118 and the drawing punch 104, as illustrated in FIG. 14.

Figure 15:
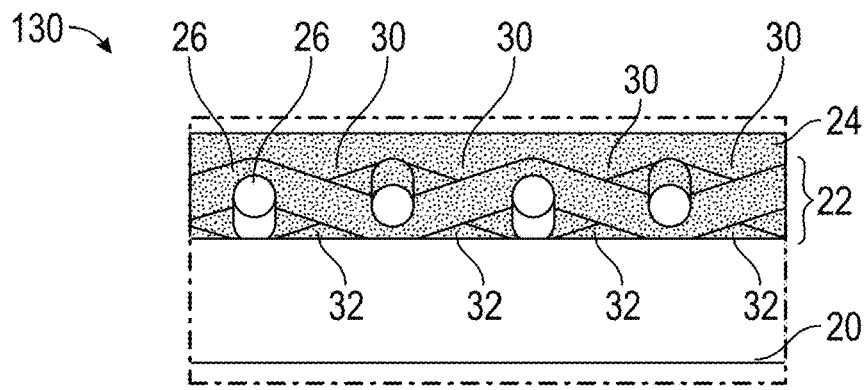
FIG. 15 illustrates a cross-sectional view of the dental blank after the coating step.

Once the desired drawing depth for the first deep-drawing process is reached, the spindle sleeves 110 are moved back into their upper starting position with the supporting plate 108 arranged thereon and the sheet metal holder 106 and the deep-drawing die set 100 is opened in that the drawing member 114 is moved further along the direction of drawing 112 upwards into its upper starting position, as illustrated in FIG. 15.

As a result, the drawn part 128 formed during the first deep-drawing process is accessible from outside the deep-drawing die set 100 and can be removed from it. There are often successive deep drawing die sets that continue to form the drawn part 128 to the final desired dimensions. The drawn part 128 may then be converted into a dental crown 10 of the present invention by trimming the excess flange around the portion that contacted the sheet metal holder 106.

After the retention layer 22 and metal base layer 20 are bonded, they are coated with a polymeric composition to form a dental blank 130. FIG. 15 illustrates a cross section of the finished dental blank 130. The polymeric composition is applied over the top of the retention layer 22, into the interstitial regions 32, around the metal strands 26 and in contact with the metal base layer 20 to form a coating 24. Afterwards, the coating 24 may be hardened to mechanically bond the coating to the metal base layer 20, especially via retention layer 22. The hardened composition in the interstitial regions 32 adjacent the metal strands 26 and metal layer 20 assist in adhering the coating to the base layer. After hardening, the coating is mechanically bonded to the metal layer 20 by the coating being locked into place within interstitial regions 32 and around the metal strands 26. However, the coating, mesh, and base combination are still flexible enough to be shaped and crimped easily by a dentist. The retention layer 22 also provides strength and flexibility.

Optionally, to increase the bonding of the coating 34 to the retention layer 22 and to metal base layer 20, both layers may be sandblasted or primed prior to the coating process.

One way to apply the esthetic layer 24 is to electrostatically apply powder to the metal retention layer 22 and base layer 20. One example of suitable powder is ALESTA epoxy-polyester hybrid, which is commercially available from Axalta Coating Systems based in Houston, Texas.

The hardenable compositions of the present disclosure are typically hardenable due to the presence of a polymerizable component. As used herein, the term "hardenable" refers to a material that can be cured or solidified, e.g., by heating to remove solvent, heating to cause polymerization, chemical crosslinking, radiation-induced polymerization or crosslinking, or the like.

In some embodiments, the compositions can be hardened (e.g., polymerized by heat, conventional photopolymerization and/or chemical polymerization techniques) after it has been applied to the surface of a dental article.

In certain embodiments, the compositions are photopolymerizable, i.e., the compositions contain a photoinitiator system that upon irradiation with actinic radiation initiates the polymerization (or hardening) of the composition. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions.

In other embodiments, the compositions are thermally polymerizable, i.e., the compositions contain a thermal initiator system that upon heating or other application of thermal energy initiates the polymerization (or hardening) of the composition.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

The polymerizable component typically comprises one or more ethylenically unsaturated compounds, with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof. The polymerizable component may comprise one or more ethylenically unsaturated compounds, with or without acid functionality that is phosphorylated, such as a phosphorylated methacrylate. In some embodiments, the polymeric composition comprises a polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

One suitable coating is taught as microparticle coating in U.S. Pat. No. 9,044,292, "Dental Articles include a Ceramic and Microparticle Coating, and Method of Making the Same," which is hereby incorporate by reference.

In one embodiment, the composition is a polymer or copolymer chosen from epoxy, polyester, and hybrids thereof. In another embodiment, the composition may be a thermoplastic polymer. If so, the thermoplastic polymer could be from polyetheretherketone (PEEK), polyaryletherketone (PAEK), polyphenolsulfones, polyethersulfones, polyacrylamide, PTFE or combinations thereof.

Preferably, the coating composition is retained on the metal shell with a minimum bond strength of at least 5 MPa. This is to provide a dental crown that will endure the various forces applied to it while the patient is chewing.

In one preferred embodiment, the metal shell has a thickness in the range of 50 to 250 micrometers. In a more preferred embodiment, the metal shell 20 has a thickness in the range of 50 to 150 micrometers. In another preferred embodiment, the coating retention layer 22 has a thickness in the range of 50 to 125 micrometers. Overall, the dental crown 10 has a thickness in the range of 50 to 700 micrometers. Such preferred thickness ranges provide flexibility and durability.

Figure 16A:
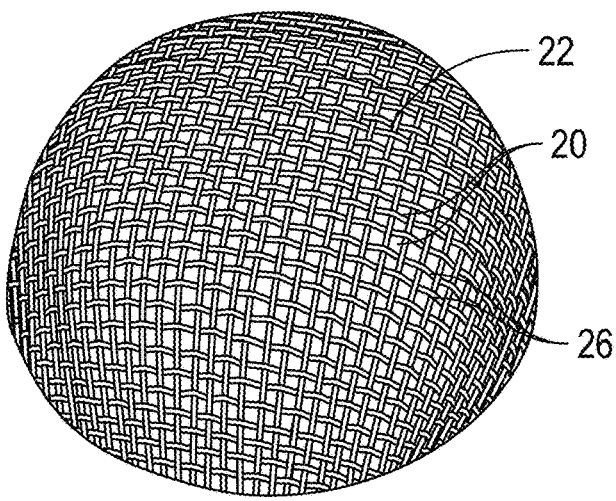
FIGS. 16A and 16B illustrate one embodiments of the metal shell after the forming process and coating process, respectively.
Figure 16B:
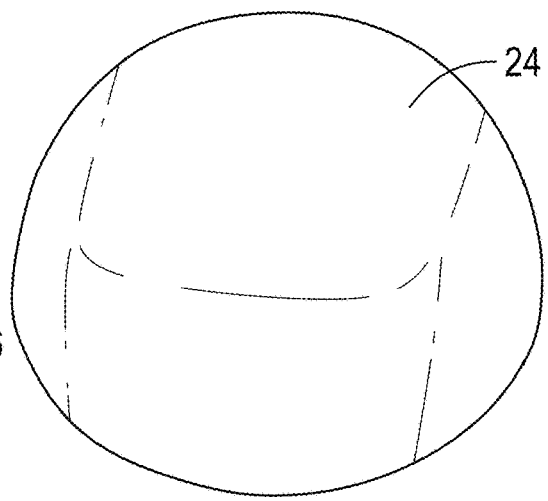
Figure 17A:
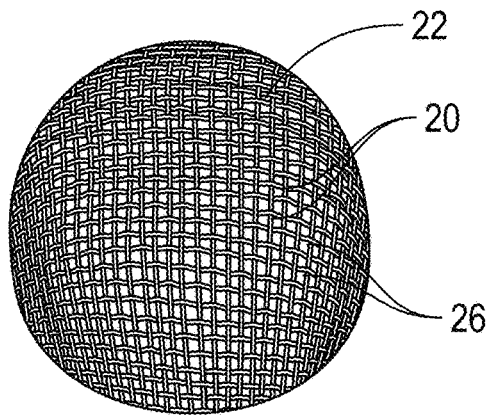
FIGS. 17A and 17B illustrates embodiment of the dental crown of the present invention after the coating process, respectively.
Figure 17B:
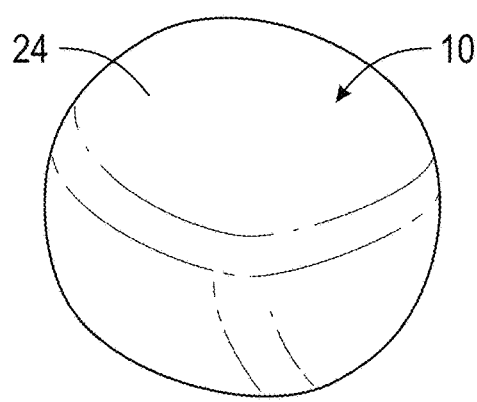

FIGS. 16A and 17A show examples of dental crowns 128 after the deep drawing process step described above, but prior to the coating process step. FIGS. 16B and 17B show examples of dental crowns after both the deep drawing process and coating process steps. Typically, the top or occlusal surface of the dental crown 10 will include grooves, indentations and or dimples (not shown), similar to normal dentition. The occlusal surface is shaped into the metal base layer 20 as part of the deep drawing process described in FIGS. 11-14, prior to the bonding and coating processes described above.

Figure 18A:
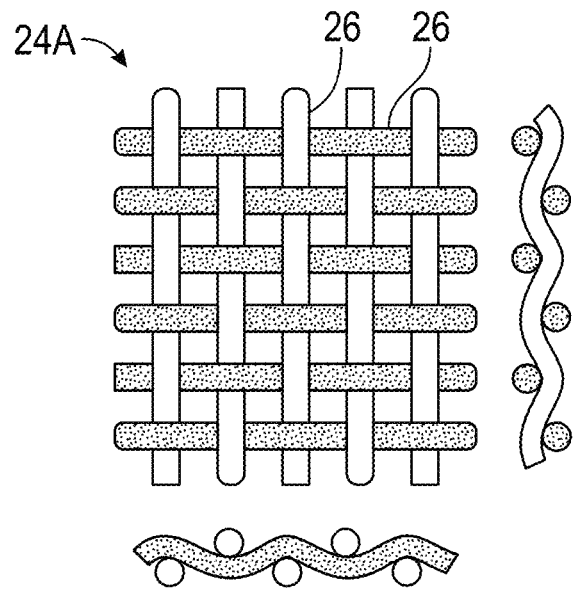
FIGS. 18A-18D illustrate various embodiments of the coating retention layer.
Figure 18B:
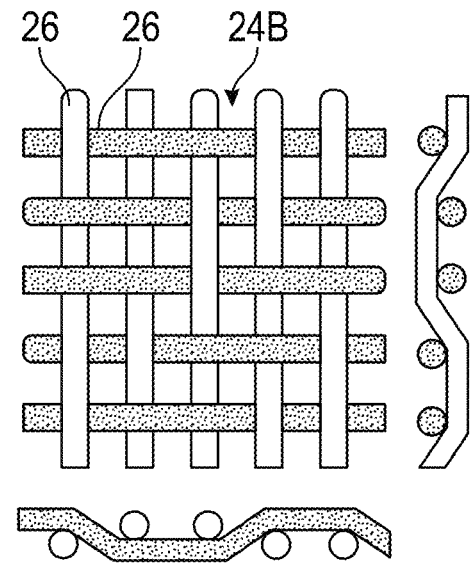
Figure 18C:
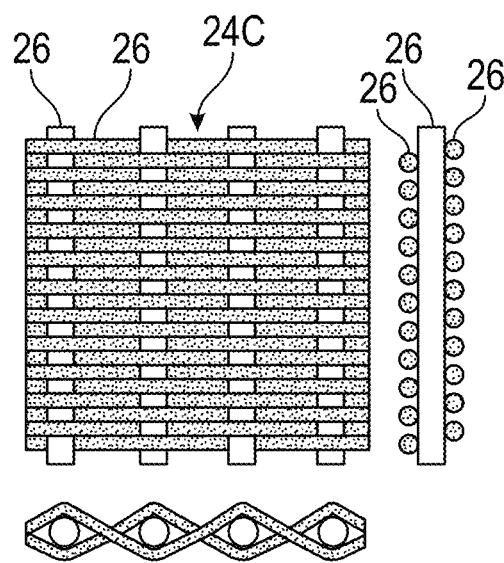
Figure 18D:
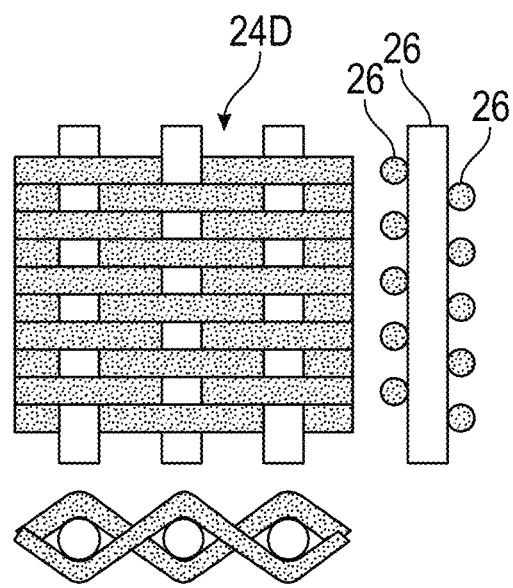

FIGS. 18A-D illustrate several examples of exemplary coating retention layer 22 having different wire mesh weave styles. FIG. 18A illustrates a plain weave style. For example, the mesh layer 22 shown in FIGS. 16A and 7A have a plain weave style. FIG. 18B illustrates a twill square weave style. FIG. 18C illustrates a reverse plain Dutch weave style. FIG. 18D illustrates a plain Dutch weave style. The coating retention layer 22 in FIGS. 18A and 18B has apertures 30 that comprise between 40 and 50 percent of the area of the coating retention layers. The coating retention layer 22 in FIGS. 18C and 18D has apertures 30 that comprise between 1 and 10 percent of the area of the coating retention layers.

The following embodiments are intended to be illustrative of the present disclosure and not limiting.

EXEMPLARY EMBODIMENTS

Embodiment 1 is a dental crown comprising: a metal shell shaped to cover a portion of a tooth of a patient; a coating retention metal layer diffusion bonded to the metal shell, wherein an interface between the coating retention layer and the metal shell comprises a plurality of interstitial regions; and a composition on the coating retention layer and within the plurality of the interstitial regions to bond the coating composition to the metal shell.

Embodiment 2 is the dental crown of embodiment 1, wherein the coating retention layer comprises an interwoven mesh, the mesh comprising a plurality of elongated metal strands, and the interstitial regions underlie at least a portion of the strands.

Embodiment 3 is the dental crown of embodiment 2, wherein a plurality of apertures between the plurality of elongated metal strands comprise 10 to 60 percent of the area of the coating retention layer.

Embodiment 4 is the dental crown of embodiment 3, wherein the open spaces between the elongated metal strands comprise 30 to 40 percent of the area of the coating retention layer.

Embodiment 5 is the dental crown of Embodiments 1, 3 and 4, wherein the coating retention layer comprises a nonwoven mesh of elongated metal strands, and the interstitial regions underlie at least a portion of the strands.

Embodiment 6 is the dental crown of Embodiments 1-5, wherein the coating composition is hardened or cured by heating to remove solvent, heating to cause polymerization, chemical crosslinking, radiation-induced polymerization or crosslinking.

Embodiment 7 is the dental crown of Embodiments 1-6, wherein the composition comprises a polymer or copolymer chosen from epoxy, polyester, and hybrids thereof.

Embodiment 8 is the dental crown of claims 1-7, wherein the composition comprises a thermoplastic polymer.

Embodiment 9 is the dental crown of Embodiment 8, wherein the composition comprises a thermoplastic polymer chosen from polyetheretherketone (PEEK), polyaryletherketone (PAEK), polyphenolsulfones, polyethersulfones, polyacrylamide, PTFE and combinations thereof.

Embodiment 10 is the dental crown of Embodiments 1-9, wherein the metal shell and/or the coating retention layer comprise stainless steel alloys.

Embodiment 11 is the dental crown of Embodiments 1-10, wherein the coating composition is retained on the metal shell with a minimum bond strength of 5 MPa.

Embodiments 12 is the dental crown of Embodiments 1-11, wherein the composition comprises a polymerizable component selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

Embodiment 13 is the dental crown of Embodiments 1-12, wherein the metal shell has a thickness in the range of 50 to 250 micrometers.

Embodiment 14 is the dental crown of Embodiments 1-13, wherein the metal shell has a thickness in the range of 50 to 150 micrometers.

Embodiment 15 is the dental crown of Embodiments 1-14, wherein the coating retention layer has a thickness in the range of 50 to 125 micrometers.

Embodiment 16 is the dental crown of Embodiments 1-15, wherein the dental crown has a thickness in the range of 50 to 700 micrometers.

Embodiment 17 is the dental crown of Embodiments 1-16, wherein the metal shell is a continuous, nonporous layer of metal.

Embodiment 18 is the dental crown of claims 1-17, wherein the composition comprises powder.

Embodiment 19 is a dental crown comprising: a continuous, nonporous metal shell shaped to cover a portion of a tooth of a patient; a coating retention metal layer of elongated metal strands bonded to the metal shell, wherein there are apertures between the elongated metal strands, wherein the apertures between the elongated metal strands comprise 10 to 60 percent of the area of the coating retention layer, and wherein an interface between the coating retention layer and the metal shell comprises a plurality of interstitial regions; and a polymeric composition on the coating retention layer and within a plurality of the interstitial regions to bond the coating composition to the metal shell.

Embodiment 20 is the dental crown of Embodiment 19, wherein the plurality of apertures between the elongated metal strands comprise 30 to 40 percent of the area of the coating retention layer.

Embodiment 21 is the dental crown of Embodiments 19-20, wherein the coating retention layer comprises an interwoven mesh, the mesh comprising a plurality of elongated metal strands, and the interstitial regions underlie at least a portion of the strands.

Embodiment 22 is the dental crown of Embodiments 19-20, wherein the coating retention layer comprises a nonwoven mesh of elongate metal strands, and the interstitial regions underlie at least a portion of the strands.

Embodiment 23 is the dental crown of Embodiments 19-22, wherein the composition is hardened or cured by heating to remove solvent, heating to cause polymerization, chemical crosslinking, radiation-induced polymerization or crosslinking.

Embodiment 24 is the dental crown of Embodiments 19-23 wherein the composition is photocurable.

Embodiment 25 is the dental crown of Embodiments 19-24, wherein the composition comprises a polymer or copolymer chosen from epoxy, polyester, and hybrids thereof.

Embodiment 26 is the dental crown of Embodiments 19-25, wherein the coating composition comprises a thermoplastic polymer.

Embodiment 27 is the dental crown of Embodiment 26, wherein the coating comprises a thermoplastic polymer chosen from polyetheretherketone (PEEK), polyaryletherketone (PAEK), polyphenolsulfones, polyethersulfones, polyacrylamide, PTFE and combinations thereof.

Embodiment 28 is the dental crown of Embodiments 19-27, wherein the metal shell and/or the coating retention layer comprise stainless steel alloys.

Embodiment 29 is the dental crown of Embodiments 19-28, wherein the composition is retained on the metal shell with a minimum bond strength of 5 MPa.

Embodiment 30 is the dental crown of Embodiments 19-29, wherein the polymeric composition comprises a polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

Embodiment 31 is the dental crown of Embodiments 19-30, wherein the metal shell has a thickness in the range of 50 to 250 micrometers.

Embodiment 32 is the dental crown of Embodiments 19-31, wherein the metal shell has a thickness in the range of 50 to 150 micrometers.

Embodiment 33 is the dental crown of Embodiments 19-32, wherein the coating retention layer has a thickness in the range of 50 to 125 micrometers.

Embodiment 34 is the dental crown of Embodiments 19-33, wherein the dental crown has a thickness in the range of 50 to 700 micrometers.

Embodiment 35 is the dental crown of Embodiments 19-34, wherein the metal shell is a continuous, nonporous layer of metal.

Embodiment 36 is the dental crown of Embodiments 19-35, wherein the composition comprises powder.

Embodiment 37 is a method of forming a dental crown, comprising: diffusion bonding a metal base layer to a coating retention layer to form a dental crown blank, wherein the coating retention layer comprises a plurality of apertures wherein an interface between the metal base layer and the coating retention layer comprises a plurality of interstitial regions; coating a composition on the coating retention layer and within the plurality of the interstitial regions to bond the coating composition to the metal base layer; and forming the dental crown blank into a dental crown shaped to cover at least a portion of a tooth of a patient.

Embodiment 38 is the method of Embodiment 37, wherein the forming step comprises pressing the blank through a die.

Embodiment 39 is the method of Embodiments 37-38, wherein the forming step comprises deep drawing the blank according to DIN 8584-3.

Embodiment 40 is the method of Embodiments 37-39, wherein the coating retention layer comprises a mesh of interwoven elongate metal strands, and wherein the plurality of interstitial regions is between the metal strands and the base layer.

Embodiment 41 is the method of Embodiments 37-40, further comprising hardening the coating composition to form a coating overlying at least a portion of the coating retention layer.

Embodiments 42 is the method of Embodiments 37-41, wherein the coating step includes electrostatically powder coating the retention layer and heating.

Embodiment 43 is the method of Embodiments 37-42, wherein the composition is hardened or cured by heating to remove solvent, heating to cause polymerization, chemical crosslinking, radiation-induced polymerization or crosslinking.

Embodiment 44 is the method of Embodiments 37-43, wherein the thermoplastic composition comprises a polymer or copolymer chosen from epoxy, polyester, and hybrids thereof.

Embodiment 45 is the method of Embodiments 37-44, wherein the coating comprises a thermoplastic polymer.

Embodiment 46 is the method of Embodiments 37-45, wherein composition comprises a thermoplastic polymer, and wherein the thermoplastic polymer is chosen from polyetheretherketone (PEEK), polyaryletherketone (PAEK), polyphenolsulfones, polyethersulfones, polyacrylamide, PTFE, and combinations thereof.

Embodiment 47 is the method of Embodiments 37-46, wherein the composition comprises a polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

Embodiment 48 is the method of Embodiments 37-47, wherein the plurality of apertures between the elongated metal strands comprise 10 to 70 percent of the area of the coating retention layer.

Embodiment 49 is the dental crown of Embodiment 48, wherein the plurality of apertures between the elongated metal strands comprise 30 to 40 percent of the area of the coating retention layer.

Embodiment 50 is the method of Embodiments 37-49, wherein at least one of the metal base layer and the coating retention layer comprise a stainless-steel alloy, or wherein both the metal base layer and the coating retention layer comprise stainless steel alloys.

Embodiment 51 is the method of Embodiments 37-50, wherein the coating retention layer comprises a nonwoven mesh of elongate metal strands, and the interstitial regions underlie at least a portion of the strands.

Embodiment 52 is the method of Embodiments 37-51, wherein the coating composition is retained on the metal shell with at least a bond strength of 5 MPa.

Embodiment 53 is the method of Embodiments 37-51, further comprising: selecting the dental crown of claim 1 to cover a tooth portion of a patient; customizing the dental crown for the patient; and attaching the dental crown to the tooth of the patient.

Embodiment 54 is a method of forming a dental crown, comprising: bonding a continuous, nonporous metal base layer to a coating retention layer to form a dental crown blank, wherein the coating retention layer comprises a plurality of apertures wherein an interface between the metal base layer and the coating retention layer comprises a plurality of interstitial regions, wherein the plurality of apertures between the elongated metal strands comprise 10 to 70 percent of the area of the coating retention layer; and coating a composition on the coating retention layer and within the plurality of interstitial regions to bond the coating composition to the metal base layer; and forming the dental crown blank into a dental crown shaped to cover at least a portion of a tooth of a patient.

Embodiment 55 is the method of Embodiment 54, wherein the plurality of apertures comprises 30 to 40 percent of the area of the coating retention layer.

Embodiment 56 is the method of Embodiments 54-55, wherein the forming step comprises pressing the blank through a die.

Embodiment 57 is the method of Embodiments 54-56, wherein the forming step comprises deep drawing the blank according to DIN 8584-3.

Embodiment 58 is the method of Embodiments 54-57, wherein the coating retention layer comprises a mesh of interwoven elongate metal strands, wherein the plurality of apertures is between the plurality of metal strands, and wherein the plurality of interstitial regions between the metal strands and the base layer.

Embodiment 59 is the method of Embodiments 54-58, further comprising hardening the composition on the coating retention layer.

Embodiment 60 is the method of Embodiments 54-59, wherein the composition is hardened or cured by heating to remove solvent, heating to cause polymerization, chemical crosslinking, radiation-induced polymerization or crosslinking.

Embodiment 61 is the dental crown of Embodiments 54-60, wherein the composition comprises a polymerizable component is selected from the group consisting of phenoxyethyl methacrylate, urethane dimethacrylate, polyethylene glycol methacrylate, polypropylene glycol methacrylate, triethyleneglycol dimethacrylate, the diglycidyl methacrylate of bisphenol A, and combinations thereof.

Embodiment 62 is the method of Embodiments 54-61, wherein the composition comprises a polymer or copolymer chosen from epoxy, polyester, and hybrids thereof.

Embodiment 63 is the method of Embodiments 54-62, wherein the coating composition comprises a thermoplastic polymer, and wherein the thermoplastic polymer is chosen from polyetheretherketone (PEEK), polyaryletherketone (PAEK), polyphenolsulfones, polyethersulfones, polyacrylamide, PTFE, and combinations thereof.

Embodiment 64 is the method of Embodiments 54-63, wherein at least one of the metal base layer and the coating retention layer comprise a stainless-steel alloy, or wherein both the metal base layer and the coating retention layer comprise stainless steel alloys.

Embodiment 65 is the method of Embodiments 54-64, wherein the coating retention layer comprises a nonwoven mesh of elongate metal strands, and the interstitial regions underlie at least a portion of the strands.

Embodiment 66 is the method of Embodiments 54-65, wherein the coating composition is retained on the metal shell with a minimum bond strength of 5 MPa.

Embodiment 67 is the method of Embodiments 54-66, wherein the bonding step includes diffusion bonding the metal base layer to the coating retention layer.

Embodiment 68 is the method of Embodiment 67, wherein diffusion bonding comprises heat and pressure.

Embodiment 69 is the method of Embodiments 54-68, wherein the coating step includes electrostatically powder coating the retention layer and heating.

Embodiment 70 is the method of claim 54-69, further comprising: selecting the dental crown of Embodiment 19 to cover a tooth portion of a patient; customizing the dental crown for the patient; and attaching the dental crown to the tooth of the patient.

Advantages and embodiments of this invention are further illustrated by the following examples, but the particular materials and amounts thereof recited in these examples, as well as other conditions and details, should not be construed to unduly limit this invention. All parts and percentages are by weight unless otherwise indicated.

EXAMPLES

Materials and Equipment

1. Stainless steel foil/mesh laminate was made by diffusion bonding a thin foil sheet to a woven wire mesh. The 304-L stainless steel plain/double style woven wire mesh was 80 Mesh (80 openings per inch) with wire thickness diameter of 94 micrometers (3.7 mil), the open area between the woven wires was approximately 300×300 micrometers, and a woven mesh layer had a thickness (pre-calendared) of approximately 135 micrometers. The 304-L stainless steel foil was 178 micrometers thick. Test portions of the laminate were cut to 2.5 cm×2.5 cm square pieces.
2. 3M FILTEK Supreme Ultra Flowable Restorative, A2 shade, available from 3M Company, St. Paul, MN, USA.
3. RAL 9001 Cream—Polyester TGIC Weather Resistant Powder Coating, available from Powder Buy the Pound, Nolensville, TN, USA.
4. 3M RelyX Ceramic Primer, Catalog Number 2721, available from 3M Company, St. Paul, MN, USA.
5. 3M ROCATEC-PLUS sandblasting material, available from 3M ESPE, Seefeld Germany.
6. 3M ELIPAR DeepCure-S LED Curing Light, available from 3M Company, St. Paul, MN, USA
7. Disc mold: A "button-shaped" mold form was made of polytetrafluoroethylene (PTFE) material with a 5-millimeter diameter circular opening, with 2-millimeter thick/deep opening. This mold was used to form a layer of composite material onto an example test surface.
8. INSTRON testing machine (Instron 5944), available from Instron Corp. Canton, Mass, USA.

Example 1

A 2.5 cm×2.5 cm square piece of the diffusion bonded stainless steel foil/mesh laminate was coated with 3M FILTEK Supreme Ultra Flowable Restorative and light cured using a 400-500 nm visible curing light. The cured restorative composite material adhered well to the substrate.

Example 2

Dental crown structures were simulated in the form of simple hemispherical caps, such as those shown in FIGS. 16A and 17A. A 2.5 cm×2.5 cm square piece of the diffusion bonded stainless steel foil/mesh laminate was formed into a hemispherical cap using a simple punch die to simulate a deep-drawing process. The deep-drawing process is used in manufacturing to create commercially available preformed stainless-steel crowns from 304-L SS foils. These formed caps were dry-powder coated with an electrostatic spraying process and using the following powder: RAL 9001 Cream—Polyester TGIC Weather Resistant Powder Coating. The caps were first washed with cleaning solution and rinsed with water prior to electrostatic coating. After the application of the powder coating, the caps were baked at 400° F. (204° C.) for 10 minutes. The final coating was approximately 125 micrometers thick.

Example 3

The mesh side of a 2.5 cm×2.5 cm square piece of the diffusion bonded stainless steel foil/mesh laminate was cleaned with acetone. The disc mold was lined with a gelatin capsule through the hole of the PTFE mold and then cut flush with a razor to the top and bottom surface of the mold, thus making a gelatin sleeve to line the mold. The gelatin sleeve will dissolve when exposed to water and this will facilitate easy removal later of the mold without disrupting the cured composite material. The disc-shaped mold with gelatin sleeve was clamped onto the mesh side of the foil/mesh laminate the metal piece. Then, FILTEK Supreme Ultra Flowable Restorative composite material was directly extruded from the syringe (with the tip immersed in the material to prevent bubbles) into the mold hole and onto the mesh side of the foil/mesh laminate. The composite material was then pressed with a spatula to make it the same level as the mold. The excess composite material was removed with spatula. The composite material was cured using the 3M ELIPAR DeepCure-S LED curing light for 30 seconds. Then the composite material bonded to the mesh side of the laminate was placed in 37° C. water for 24 hours before testing the bonding strength. The final test object of Example 3 was a 2.5 cm square piece of the SS foil/mesh laminate with a circular button/disc (5 millimeter in diameter and 2-millimeter-thick) of composite material bonded to the mesh side of the SS foil/mesh laminate.

Comparative Example 1

Comparative Example 1 was prepared in the same manner as Example 3 except that the foil side of the foil/mesh laminate was cleaned with acetone and the FILTEK Supreme Ultra Flowable Restorative composite material was applied and cured to the foil side of a stainless-steel foil/mesh laminate sheet.

Comparative Example 2

Comparative Example 2 was prepared in the same manner as Comparative Example 1, except that the foil side of the foil/mesh laminate was first sandblasted with 3M ROCATEC-PLUS sandblasting material and then cleaned with acetone. Finally, FILTEK Supreme Ultra Flowable Restorative composite material was applied and cured to the sandblasted prepared foil side of a stainless-steel foil/mesh laminate sheet.

Comparative Example 3

Comparative Example 3 was prepared in the same manner as Comparative Example 2, except that after the foil side of the foil/mesh laminate was sandblasted and then cleaned with acetone and dried, and then further a primer layer of 3M RelyX Ceramic Primer was applied for 20 seconds to the sandblasted, cleaned foil side of the laminate, followed by air drying of the primer. Finally, FILTEK Supreme Ultra Flowable Restorative composite material was applied and cured to the sandblasted and primer prepared foil side of a stainless-steel foil/mesh laminate sheet.

Shear Bond Strength Testing:

Shear bond strength of the composite material to the metal substrate was measured for Example 3, and Comparative Examples 1-3 according to the following procedure. Each example was prepared and tested with 5 replicates. Prior to the shear bond strength testing the PTFE disc mold was removed. The shear bond strength of a cured test examples was evaluated by clamping one end of the metal laminate in the jaws of an INSTRON testing machine (Instron 5944) with the metal surface oriented parallel to the direction of push. A notched-edge fixture (hemispherical in shape, designed to fit and engage one half of the composite button/disc) was placed around the cured composite material button adjacent to the metal surface. After alignment, the notched-edge fixture was clamped in the travelling jaw of the INSTRON apparatus and pushed at a crosshead speed of 1 millimeter per minute, thereby placing the adhesive bond in shear stress, with a pushing force. The force in kilograms (kg) at which the bond failed was recorded, and this number was converted to a force per unit area (units of kg/cm$^2$ or MPa) using the known surface area of the button. Additionally, each surface was observed to determine the mode failure where it was characterized as "adhesive" when there was no remnant of the cured composite material left on the metal surface, or "cohesive" when there was remnant of the cured composite material left on the metal surface. Each reported value of adhesion represents the average of 5 replicates. The values in the parentheses show the standard deviation of the five replicate measurements of shear bond strength for each example.

TABLE 1

Shear Bond Strengths of Example 3 and Comparative Examples C1, C2, and C3.

| Example | Surface to which composite material was applied and cured | Shear Bond Strength: MPa (StDev) | Failure Mode |
| --- | --- | --- | --- |
| Example 3 | Mesh side of laminate | 11.5 (4.4) | Cohesive |
| Comp. Ex. 1 | Foil side of laminate | 0 | Adhesive |
| Comp. Ex. 2 | Foil side of laminate prepared with sandblasting | 4.6 (0.3) | Adhesive |
| Comp. Ex. 3 | Foil side prepared with sandblasting and primer | 6.3 (1.6) | Adhesive |

What is claimed is:

1. A method of forming a dental crown, comprising:
   diffusion bonding a metal base layer to a coating retention layer to form a dental crown blank, wherein the coating retention layer comprises a plurality of apertures, and wherein an interface between the metal base layer and the coating retention layer comprises a plurality of interstitial regions;
   coating a composition on the coating retention layer and within the plurality of the interstitial regions to bond the coating composition to the metal base layer; and
   forming the dental crown blank into a dental crown shaped to cover at least a portion of a tooth of a patient.

2. The method of claim 1, wherein forming the dental crown blank into the dental crown comprises pressing the blank through a die.

3. The method of claim 1, wherein forming the dental crown blank into the dental crown comprises deep drawing the blank.

4. The method of claim 1, wherein the coating retention layer comprises a mesh of interwoven elongate metal strands, and wherein the plurality of interstitial regions is between the interwoven elongate metal strands and the metal base layer.

5. The method of claim 1, further comprising hardening the coating composition to form a coating overlying at least a portion of the coating retention layer.

6. The method of claim 1, wherein coating the composition on the coating retention layer and within the plurality of the interstitial regions includes electrostatically powder coating the retention layer and heating.

7. The method of claim 1, wherein the composition is hardened or cured by heating to remove solvent, heating to cause polymerization, chemical crosslinking, radiation-induced polymerization or crosslinking.

8. The method of claim 1, wherein the composition comprises a polymer or copolymer chosen from epoxy, polyester, and hybrids thereof.

9. The method of claim 1, wherein the coating comprises a thermoplastic polymer.

10. The method of claim 1, wherein composition comprises a thermoplastic polymer, and wherein the thermoplastic polymer is chosen from polyetheretherketone (PEEK), polyaryletherketone (PAEK), polyphenolsulfones, polyethersulfones, polyacrylamide, PTFE, and combinations thereof.

11. The method of claim 1, wherein the composition comprises a polymerizable component selected from at least one of phenoxyethyl methacrylate, urethane dimethacrylate, polyethylene glycol methacrylate, polypropylene glycol methacrylate, triethyleneglycol dimethacrylate, or a diglycidyl methacrylate of bisphenol A.

12. The method of claim 1, wherein the plurality of apertures comprise 10 to 70 percent of an area of the coating retention layer.

13. The method of claim 12, wherein the plurality of apertures comprise 30 to 40 percent of the area of the coating retention layer.

14. The method of claim 1, wherein at least one of the metal base layer and the coating retention layer comprise a stainless-steel alloy, or wherein both the metal base layer and the coating retention layer comprise stainless steel alloys.

15. The method of claim 1, wherein the coating composition is retained on a metal shell with at least a bond strength of 5 MPa.

16. The method of claim 1, further comprising:
   selecting the dental crown to cover a tooth portion of a patient;
   customizing the dental crown for the patient; and
   attaching the dental crown to the tooth of the patient.

17. A method of forming a dental crown, comprising:
   diffusion bonding a continuous, nonporous metal base layer to a coating retention layer to form a dental crown blank, wherein the coating retention layer comprises a plurality of apertures wherein an interface between the metal base layer and the coating retention layer comprises a plurality of interstitial regions, wherein the plurality of apertures comprise 10 to 70 percent of an area of the coating retention layer;
   coating a composition on the coating retention layer and within the plurality of the interstitial regions to bond the coating composition to the metal base layer; and
   forming the dental crown blank into a dental crown shaped to cover at least a portion of a tooth of a patient.

18. The method of claim 17, wherein the plurality of apertures comprises 30 to 40 percent of the area of the coating retention layer.

19. The method of claim 17, wherein the coating retention layer comprises a mesh of interwoven elongate metal strands, wherein the plurality of apertures is between the interwoven elongate metal strands, and wherein the plurality of interstitial regions are between the interwoven elongate metal strands and the metal base layer.

20. The method of claim 17, wherein the coating composition comprises a thermoplastic polymer, and wherein the thermoplastic polymer is chosen from at least one of polyetheretherketone (PEEK), polyaryletherketone (PAEK), polyphenolsulfones, polyethersulfones, polyacrylamide, or PTFE.

* * * * *